(12) United States Patent
Yang et al.

(10) Patent No.: US 7,898,664 B2
(45) Date of Patent: Mar. 1, 2011

(54) METHOD FOR MEASURING CHROMATICITY VALUES BY A COLORIMETER

(75) Inventors: Tsung-Hsun Yang, Jhongli (TW); Wei-Ping Lin, Jhongli (TW)

(73) Assignee: National Central University, Taoyuan County (TW)

( * ) Notice: Subject to any disclaimer, the term of this patent is extended or adjusted under 35 U.S.C. 154(b) by 288 days.

(21) Appl. No.: 11/874,994

(22) Filed: Oct. 19, 2007

(65) Prior Publication Data

US 2009/0103075 A1   Apr. 23, 2009

(51) Int. Cl.
*G01N 21/25* (2006.01)
(52) U.S. Cl. .................. 356/407; 356/406
(58) Field of Classification Search ............. 356/243.5, 356/402, 405, 406, 407
See application file for complete search history.

(56) References Cited

U.S. PATENT DOCUMENTS 7,014,336 B1* 3/2006 Ducharme et al. .......... 362/231
2001/0036309 A1* 11/2001 Hirayama et al. ........... 382/167
2006/0146326 A1* 7/2006 Nagashima et al. ......... 356/328
2008/0069439 A1* 3/2008 Kwak et al. ................. 382/162

* cited by examiner

*Primary Examiner*—Tarifur Chowdhury
*Assistant Examiner*—Tara S Pajoohi

(57) ABSTRACT

A method measures chromaticity values using a colorimeter to solve the drawbacks of conventional technologies, such as an inaccurate illuminant, the filter of color-matching function being difficult to be deposited and manufactured within a filter mod colorimeter, and using an expensive spectrometer within a spectrum mode colorimeter. The spectrometer and the filter of color-matching function is not needed, and an accurate chromaticity value of an object by using a multi-band illuminant illuminating the object and a power meter. Further, the multi-band illuminant can adjust the illumination condition of a standard illuminator under different color temperatures, and the chromaticity values of the object can be measured under different color temperatures. The accuracy of the measured chromaticity values is up to the level of the spectrum mode colorimeter, and the price is less than the spectrum mode colorimeter.

2 Claims, 9 Drawing Sheets

METHOD FOR MEASURING CHROMATICITY VALUES BY A COLORIMETER

BACKGROUND OF THE INVENTION

1. Field of the Invention

The present invention relates to a method for measuring the chromaticity values in a colorimeter and, more particularly, to a measuring method that can get the accuracy level of the measured chromaticity values up to the spectrum mode colorimeter but does not need to use the filters with color-matching functions that are difficult to be deposited and manufactured and is cheaper than the spectrum mode colorimeter.

2. Description of Related Art

A colorimeter is used to measure the data of color performance of an object in different appropriate standard lighting environments. The colorimeter can objectively measure the color of different objects, for example, the reflective surface of plastics, paint, coating, printing, etc., for achieving the control, duplication and delivery of colors effectively. Therefore, the colorimeter is one of the important instruments regardless of the industrial application or the academic research.

In order to quantify and define color by a scientific way, Commission International del'Eclairage (CIE) established a color-matching function $\bar{x}(\lambda)$, $\bar{y}(\lambda)$ and $\bar{z}(\lambda)$ under an equal energy condition in 1931. The appeared color of any illuminated object, such as the spectral intensity of an illuminant $S(\lambda)$ and the reflectance of the object $R(\lambda)$, can be calculated by the color-matching function based on XYZ color basis. The XYZ color space is named the CIE 1931 color space system. It is inconvenient in analysis and in applications to depict color coordinates on three-dimensional coordinates as getting a group of XYZ color coordinate data and considering the position in the coordinate space. Based on the concept of the luminance normalization, the equation of an xy color coordinate is first defined as $x+y+z=1$ while dealing with XYZ color coordinate. The color space defined by x and y is named CIE xy chromaticity diagram.

Nowadays, the measurement of the chromaticity values by a reflection mode colorimeter is according to the standard CIE method to compute the total energy by the reflective light of the object, the CIE color-matching function and a weighting consideration on different wavelengths. The individual chromaticity values depend on the computed total energy and the different color-matching function is obtained.

The foregoing procedure, such as the weighting of color-matching function and the summation of the stimulus energy, can be generalized and divided into two classifications at the design principle.

A. Filter Mode Colorimeter:

Referring to FIG. 7, the filter mode colorimeter cooperates with a specific standard illuminant 20, such as CIE standard illuminant A, CIE standard illuminant C, CIE standard illuminant D, etc., and the specific standard illuminant 20 illuminates on the surface of an object 21. A reflective light 22 that reflects from the surface of the object 21 passes through filters 23 of the color-match functions and is received separately by a multi-band power meter 24. The chromaticity values of the object 21 are obtained afterwards.

However, the marketed standard illuminant D is not accurate enough, and the filters 23 of the color-matching functions are difficult to be deposited and manufactured. The measured chromaticity values are not easy to measure at an accurate level.

B. Spectrum Mode Colorimeter:

Referring to FIG. 8, an object 31 is illuminated by a known white light illuminant 30, and a reflective light 32 that reflects from the surface of the object 31 is received. The reflection index of the object 31 is computed by a spectrometer 33 in a colorimeter. The chromaticity values of the object 31 illuminated on the different standard illuminants will be figured out through the calculation of the colorimeter.

However, the spectrum mode colorimeter is more expensive even though a more accurate chromaticity values of the object can be computed by the spectrum mode colorimeter.

There are some drawbacks in the conventional technologies. For example, the measured chromaticity values by the filter mode colorimeter that is equipped with the marketed standard illuminant D is not accurate enough. Besides, the filter of the color-matching function used to receive the reflective light is difficult to be deposited and manufactured and is inconvenient for mass production.

In addition, the more accurate chromaticity values are obtained through the reflective light received by the spectrometer in the spectrum mode colorimeter. However, the spectrometer is more expensive and is not agreeable to the consideration of the economic benefits.

Due to the drawbacks of the conventional colorimeters, the investigation and research was taken for solving the problems of the colorimeter based on the experiences of research and manufacture in the industrial field. Finally, a method measures the chromaticity values by a colorimeter and exactly improves the above-mentioned drawbacks.

SUMMARY OF THE INVENTION

The main objective of the present invention is to provide a method for achieving the accuracy of the measured chromaticity values up to the level of the spectrum mode colorimeter and for being less expensive than the spectrum mode colorimeter.

To achieve the objective, the present invention provides a method for measuring the chromaticity values by a colorimeter, comprising the steps of:

(a) emitting three visible band light of different spectra individually on the surface of an object 11 with a multi-band illuminant 10;

(b) forming a reflective light 13 reflecting from an illuminating light 12 on the surface of the object 11, with the reflective light 13 passing through a power meter 14 within the colorimeter; and (c) computing chromaticity values of the object by the luminous intensity that is received by the power meter.

Therefore, the present invention easily adjust the color temperature of the multi-band illuminant. Compared with the conventional filter mode colorimeter using the standard illuminant D, the chromaticity values are obtained with the accuracy level of the spectrum mode colorimeter, and the reflective light is received by the power meter to avoid the disadvantage of using the expensive spectrometer.

The present invention provides a method to measure the chromaticity values by a colorimeter and to achieve the accurate chromaticity values similar to the spectrum mode colorimeter by illuminating the object by the multi-band illuminant. Furthermore, it is less expensive than the spectrum mode colorimeter and improves the drawbacks of the filter mode colorimeter and the spectrum mode colorimeter.

Further benefits and advantages of the present invention will become apparent after a careful reading of the detailed description with appropriate reference to the accompanying drawings.

DETAILED DESCRIPTION OF THE INVENTION

Figure 1:
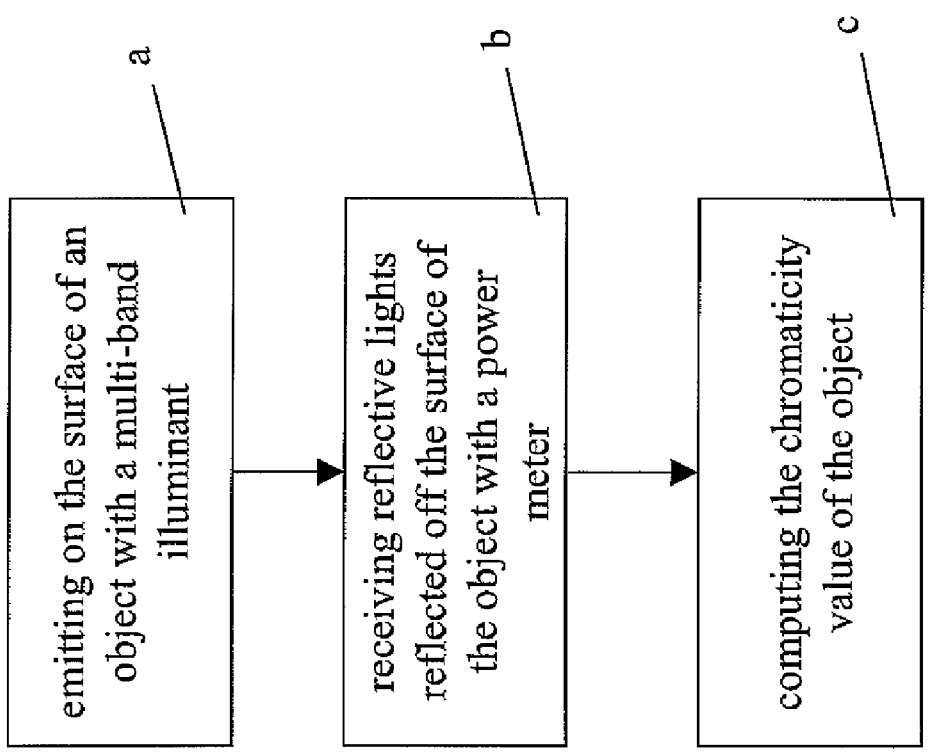
FIG. 1 is a flowchart of a method of the present invention.
Figure 2:
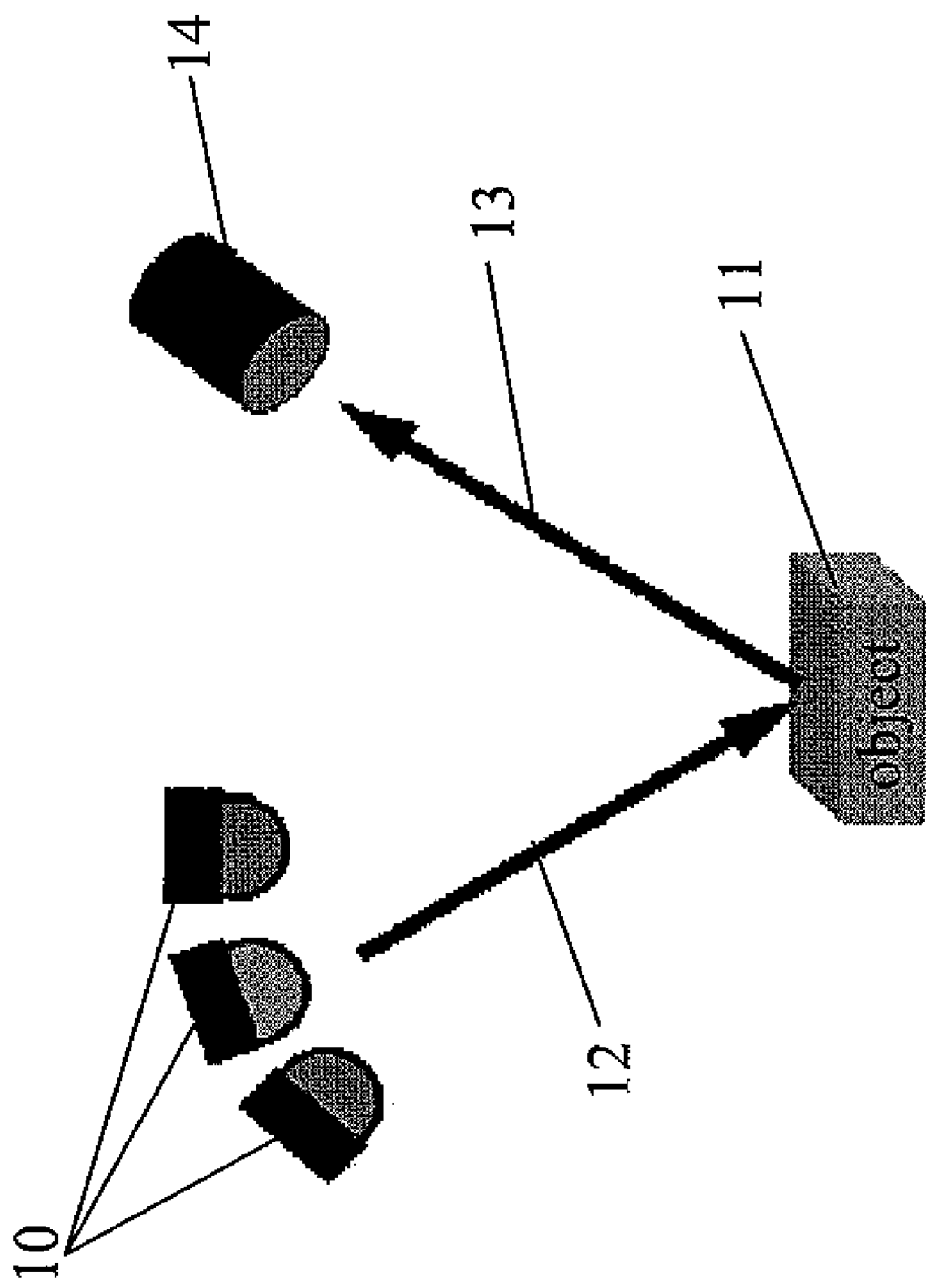
FIG. 2 is a schematic diagram of a method of the present invention.

Referring to FIG. 1 and FIG. 2, the present invention provides a method for measuring the chromaticity values by a colorimeter, comprising the steps of:

(a) emitting three visible band light of different spectra, $S(\lambda)*\bar{x}(\lambda)/PM(\lambda)$, $S(\lambda)*\bar{y}(\lambda)/PM(\lambda)$ and $S(\lambda)*\bar{z}(\lambda)/PM(\lambda)$ individually on a surface of an object 11 with a multi-band illuminant 10;

wherein the spectra $S(\lambda)*\bar{x}(\lambda)/PM(\lambda)$, $S(\lambda)*\bar{y}(\lambda)/PM(\lambda)$ and $S(\lambda)*\bar{z}(\lambda)/PM(\lambda)$ simulate a CIE standard illuminant with a certain correlated color temperature. The multi-band illuminant 10 comprises a plurality of single wavelength lights distributed in the visible light band, such as a demanded spectrum illuminant of the colorimeter including a plurality of color light emitting diode (LEDs). The amount of color LED can be 24 pieces or lesser. The demanded spectrum of the multi-band illuminant 10 will be acquired by adjusting the light intensity of each color LED.

Wherein the spectra are implemented via tuning a driving electric current going through each LED such that the combined spectra is tuned as shown in FIGS. 3, 4, 6A, and 6B.

(b) forming a reflective light 13 reflecting from an illuminating light 12 on the surface of the object 11. The reflective light 13 passes through a power meter 14 within the colorimeter, and wherein the reflective lights are with spectra of $R(\lambda)*[S(\lambda)*\bar{x}(\lambda)/PM(\lambda)]$, $R(\lambda)*[S(\lambda)*\bar{y}(\lambda)]/PM(\lambda)]$ and $R(\lambda)*[S(\lambda)*\bar{z}(\lambda)]/PM(\lambda)]$; and (c) computing the chromaticity values of the object by the luminous intensity received by the power meter.

Figure 3:
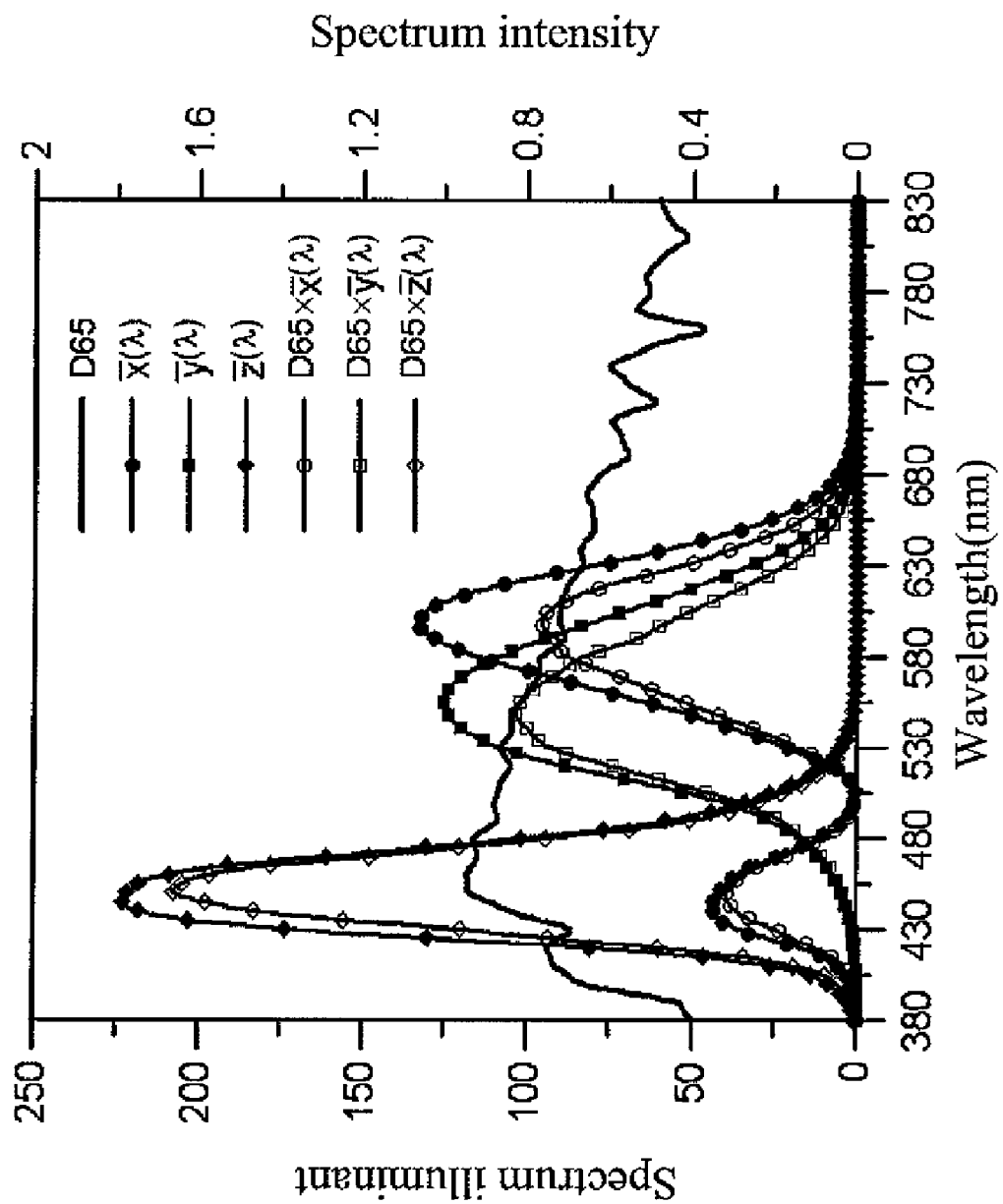
FIG. 3 is a spectral diagram showing all the spectra of the illuminant D65 and the color matching functions, $\bar{x}(\lambda)$, $\bar{y}(\lambda)$ and $\bar{z}(\lambda)$.

FIG. 3 shows the chromaticity values of object as an illuminant D65 (6504 K) illuminating on the object. To compute the product of the illuminant spectrum $S(\lambda)$ (D65 spectrum distribution), the reflectance of the object $R(\lambda)$ and CIE 1931 color-matching function, $\bar{x}(\lambda)$, $\bar{y}(\lambda)$ and $\bar{z}(\lambda)$ individually, X, Y, Z data can be obtained through integrating the product between the visible light band ($\lambda$=380 nm~830 nm).

The distributed spectrum illuminant, $S(\lambda)*\bar{x}(\lambda)$, $S(\lambda)*\bar{y}(\lambda)$ and $S(\lambda)*\bar{z}(\lambda)$, from the multi-band illuminant illuminates on the object in turn and is received by the multi-band power meter after times the reflectance of the object $R(\lambda)$, that is the same as integration. The X, Y, Z data will be obtained therefore.

Considering the frequency response of the power meter, $PM(\lambda)$, on every wavelength, the multi-band illuminant is actually further used for forming the distributed spectrum illuminant individually, such as $S(\lambda)*\bar{x}(\lambda)/PM(\lambda)$, $S(\lambda)*\bar{y}(\lambda)/PM(\lambda)$ and $S(\lambda)*\bar{z}(\lambda)/PM(\lambda)$, with:

$$X = 683 * \int \left[\frac{S(\lambda)\bar{x}(\lambda)}{PM(\lambda)}\right] R(\lambda)PM(\lambda)d\lambda$$

$$Y = 683 * \int \left[\frac{S(\lambda)\bar{y}(\lambda)}{PM(\lambda)}\right] R(\lambda)PM(\lambda)d\lambda$$

$$Z = 683 * \int \left[\frac{S(\lambda)\bar{z}(\lambda)}{PM(\lambda)}\right] R(\lambda)PM(\lambda)d\lambda,$$

The integration of $Z=683*\int \square * R(\lambda)PM(\lambda)d\lambda$ is directly operated during the detection process in the power meter.

The distributed spectrum illuminant is verified with simulations.

Figure 4:
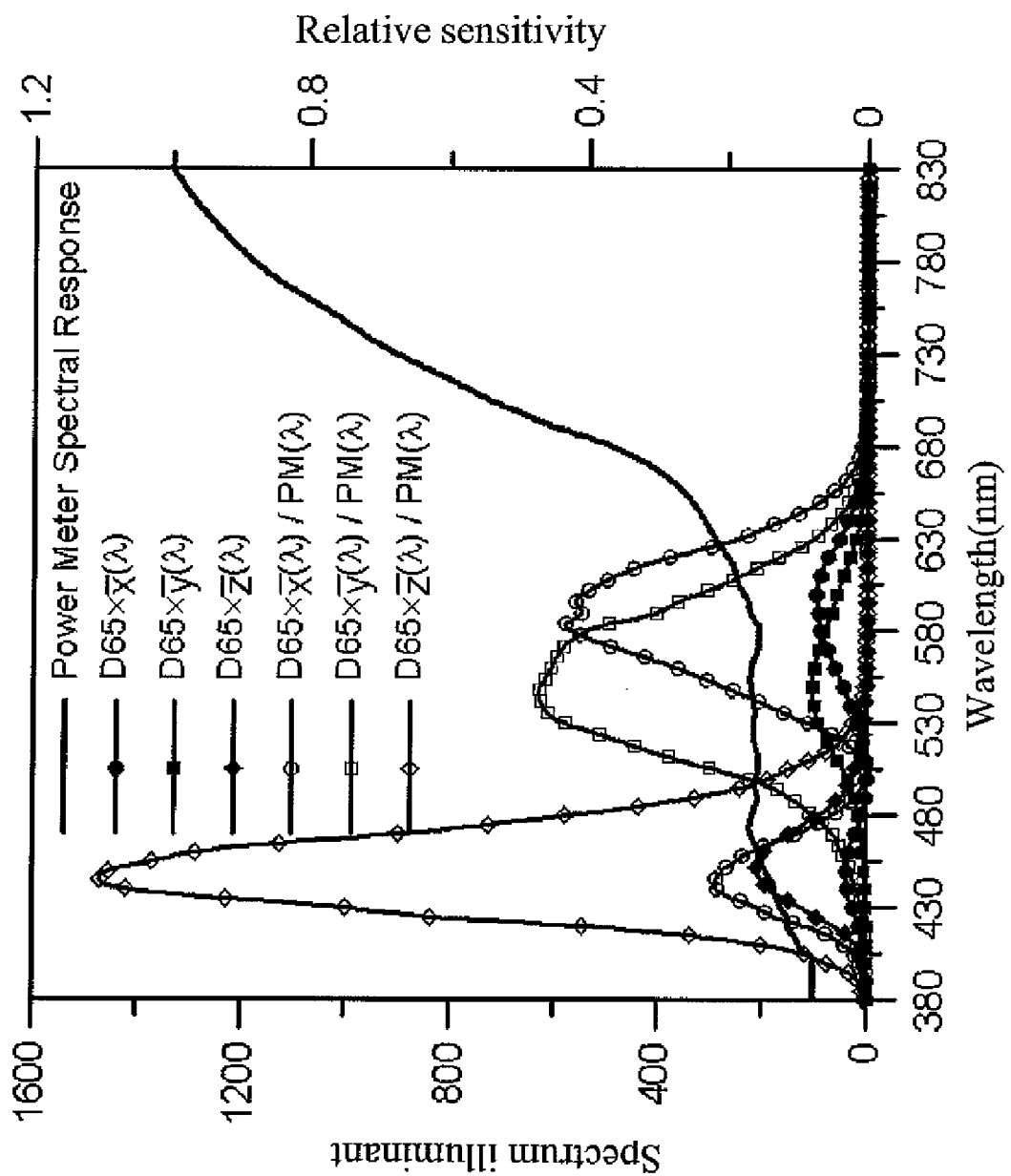
FIG. 4 is a spectral diagram showing the frequency response of the power meter and the spectra of the multi-band illuminant of D65.

As shown in FIG. 4, the multi-band illuminant produces the distributed spectrum illuminant, $D65\bar{x}(\lambda)/PM(\lambda)$, $D65\bar{y}(\lambda)/PM(\lambda)$ and $D65*\bar{z}(\lambda)/PM(\lambda)$, by adopting the frequency response $PM(\lambda)$ the power meter.

Figure 5:
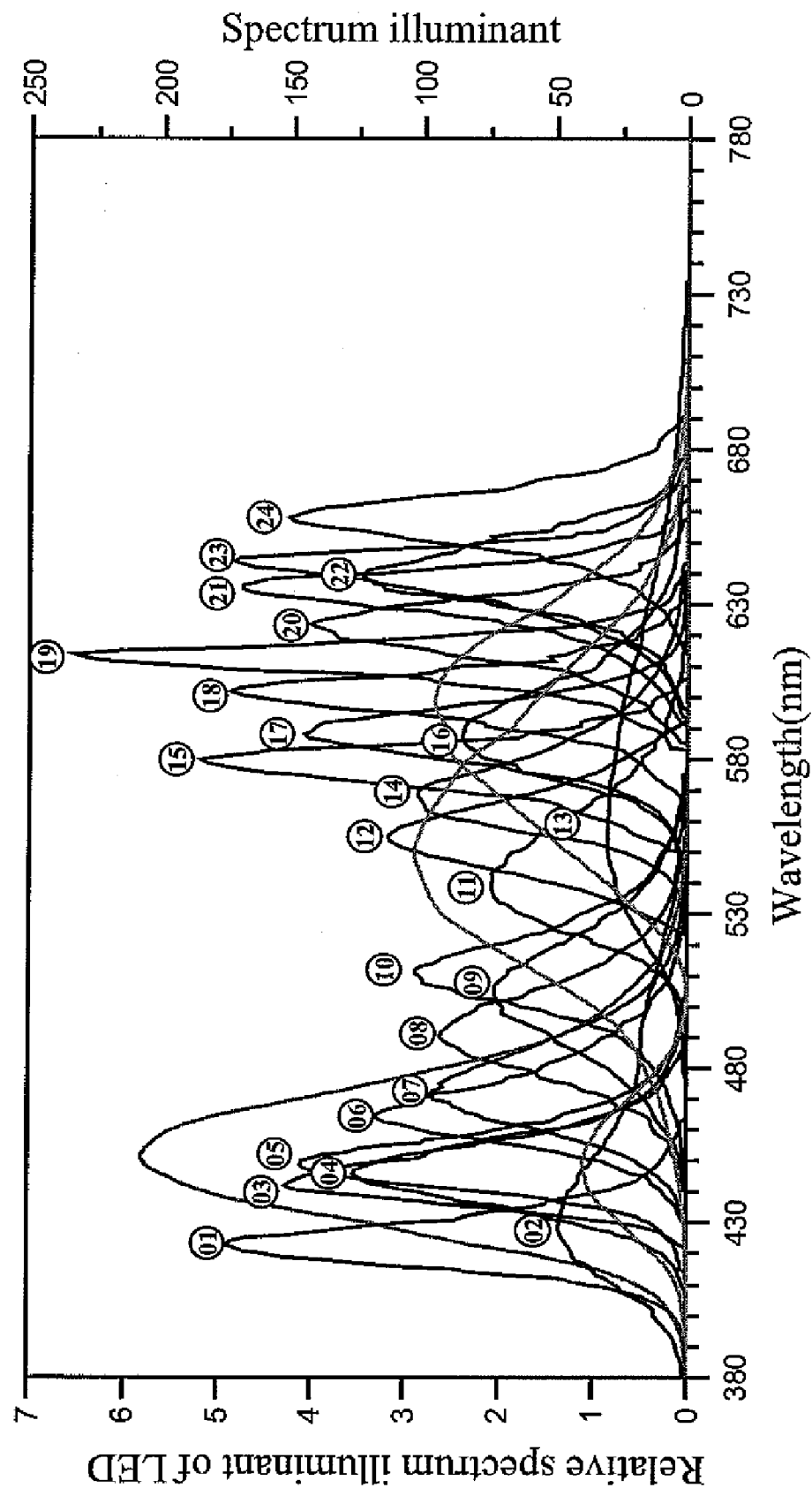
FIG. 5 is a spectrum diagram showing each the spectrum of 24 pieces of LEDs used.

Referring to FIG. 5, the light source of the multi-band illuminant is simulated to comprise 24 pieces of LED, and the spectrum distribution is between 380 nm and 730 nm.

Figure 6A:
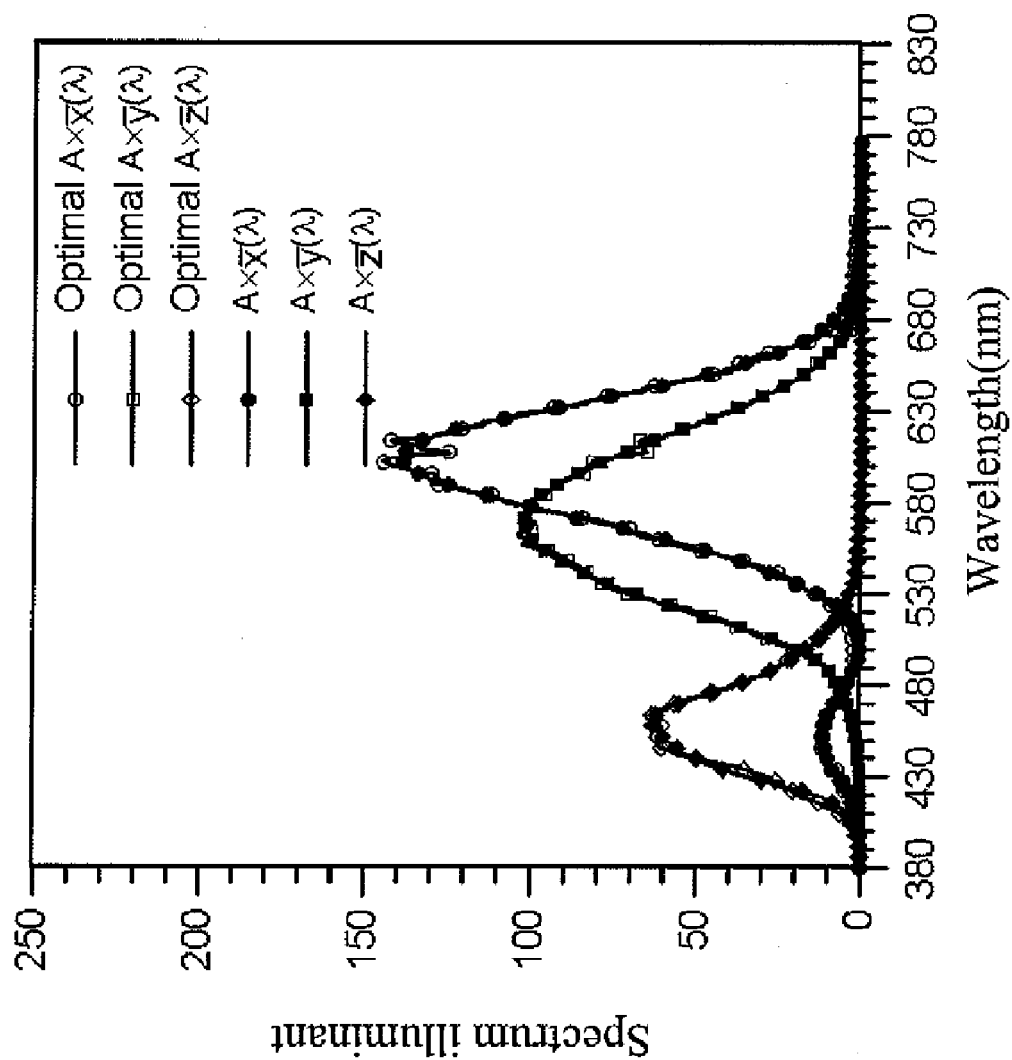
FIG. 6A is a simulation result of CIE standard illuminant A.
Figure 6B:
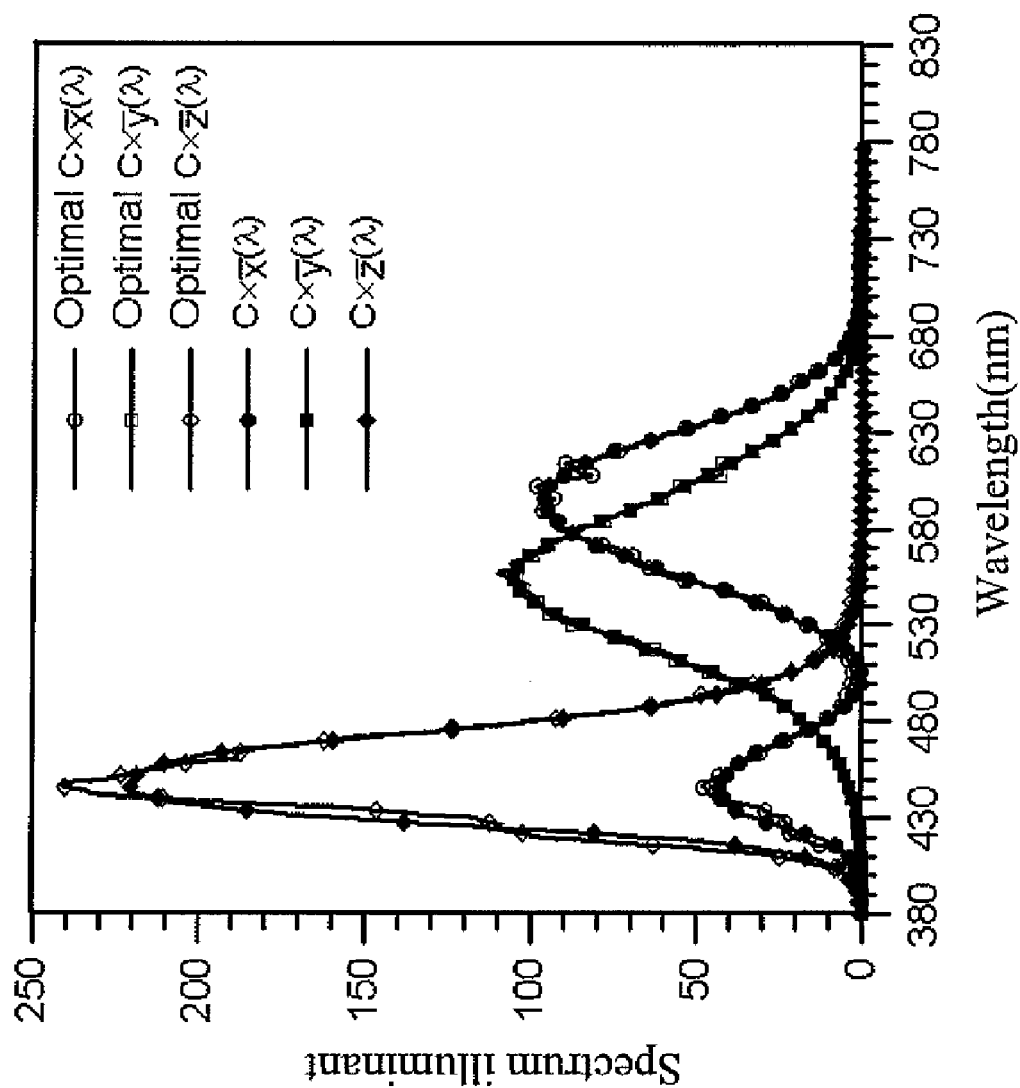
FIG. 6B is a simulation result of CIE standard illuminant C.
Figure 7:
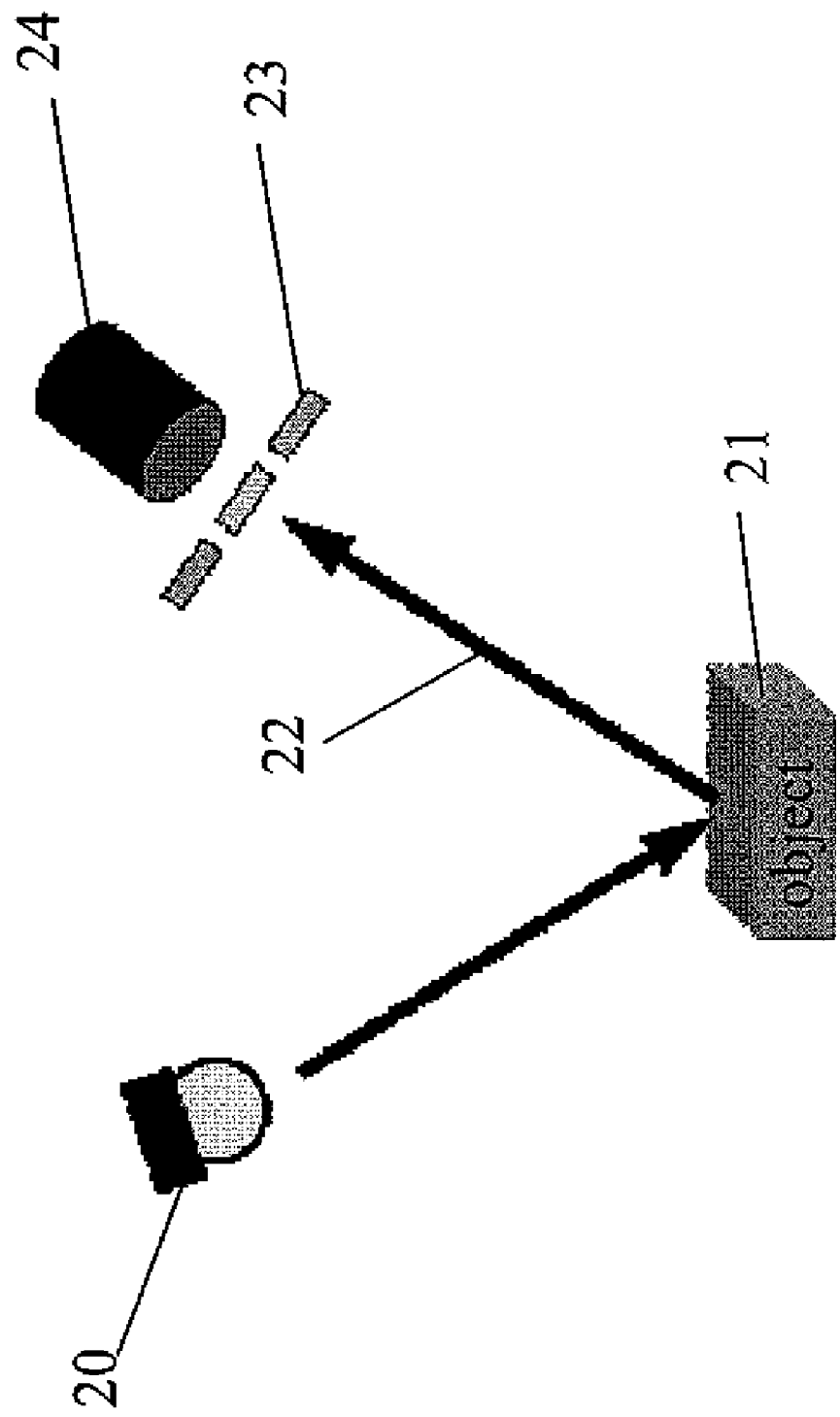
FIG. 7 is a schematic conventional filter mode colorimeter.
Figure 8:
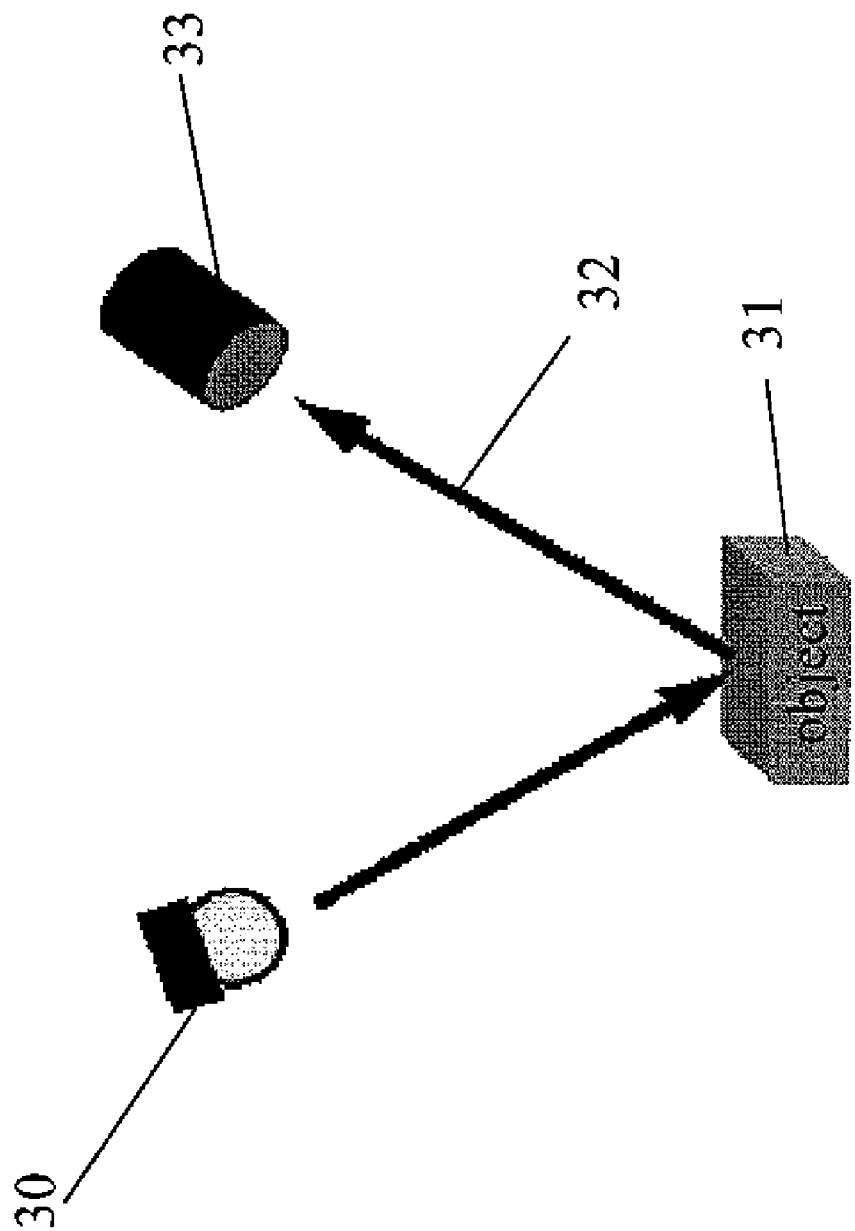
FIG. 8 is a schematic conventional spectrum mode colorimeter.

FIG. 6A and FIG. 6B, are the simulation results depended on the CIE standard illuminant A and the CIE standard illuminant C, and the simulated spectral distributions are very close to the theoretical spectral distribution.

The present invention provides a remixed illuminator as the illuminator of the colorimeter through assembled multi-band illuminants. The remixed illuminator can be adjusted directly to achieve the effect that is like the filters of the color-matching functions. Besides, the present invention does not need the spectrometer and the filters of the color-matching function and can measure the accurate chromaticity value of an object by using a multi-band illuminant illuminating the object and a power meter. The accuracy of the measured chromaticity values is up to the level of the spectrum mode colorimeter, and the price is much less than the spectrum mode colorimeter.

Moreover, the multi-band illuminant can adjust the illumination condition of the standard illuminator under different color temperatures and can directly measure the chromaticity values on the real condition, that is not like the result of the current status to be obtained through analogizing and calibrating for the different band of illuminants after illuminating and measuring by a single-band illuminant.

Although the invention has been explained in relation to its preferred embodiment, it is to be understood that many other possible modifications and variations can be made without departing from the spirit and scope of the invention as hereinafter claimed.

What is claimed is:

1. A method for measuring chromaticity values in a colorimeter, comprising:

(a) emitting three visible band light of different spectra, $S(\lambda)*\bar{x}(\lambda)/PM(\lambda)$, $S(\lambda)*\bar{y}(\lambda)/PM(\lambda)$ and $S(\lambda)*\bar{z}(\lambda)/PM(\lambda)$ individually on a surface of an object with a multi-band illuminant, wherein the multi-band illuminant comprises a plurality of color light emitting diodes (LEDs) to form the spectra, $S(\lambda)*\bar{x}(\lambda)/PM(\lambda)$, $S(\lambda)*\bar{y}(\lambda)/PM(\lambda)$ and $S(\lambda)*\bar{z}(\lambda)/PM(\lambda)$ individually based on a requested $S(\lambda)$ of a certain color temperature;

(b) receiving reflective lights reflected off the surface of the object with a power meter, wherein the power meter is calibrated to perform the function of $683*\int PM(\lambda)d\lambda$, wherein the reflective lights are with spectra of $R(\lambda)*[S(\lambda)*\bar{x}(\lambda)/PM(\lambda)]$, $R(\lambda)*[S(\lambda)*\bar{y}(\lambda)]/PM(\lambda)]$ and $R(\lambda)*[S(\lambda)*\bar{z}(\lambda)/PM(\lambda)]$;

(c) computing chromaticity values X, Y, Z of the object based upon a luminous intensity received by the power meter, wherein the power meter receives the reflective lights reflected off the surface of the object; and (d) obtaining the chromaticity values X, Y, Z that is $$X = 683 * \int \frac{S(\lambda)\bar{x}(\lambda)}{PM(\lambda)} R(\lambda) PM(\lambda) d\lambda$$

$$Y = 683 * \int \frac{S(\lambda)\bar{y}(\lambda)}{PM(\lambda)} R(\lambda) PM(\lambda) d\lambda$$

$$Z = 683 * \int \frac{S(\lambda)\bar{z}(\lambda)}{PM(\lambda)} R(\lambda) PM(\lambda) d\lambda,$$

wherein an illuminating spectrum tunes the effect of $S(\lambda)$ based upon various requested colorimetric conditions, wherein the various requested colorimetric conditions are CIE standard illuminants A and C.

2. The method as claimed in claim 1, wherein the spectra are implemented via tuning a driving electric current going through each LED such that the combined spectra are tuned.

* * * * *